United States Patent
Baril et al.

(12)

(10) Patent No.: US 11,364,051 B2
(45) Date of Patent: Jun. 21, 2022

(54) CUTTING GUARD

(71) Applicant: Covidien LP, Mansfield, MA (US)

(72) Inventors: Jacob C. Baril, Norwalk, CT (US); Saumya Banerjee, Hamden, CT (US); Roy J. Pilletere, North Haven, CT (US); Justin Thomas, New Haven, CT (US); Matthew A. Dinino, Newington, CT (US)

(73) Assignee: COVIDIEN LP, Mansfield, MA (US)

( * ) Notice: Subject to any disclaimer, the term of this patent is extended or adjusted under 35 U.S.C. 154(b) by 107 days.

(21) Appl. No.: 16/796,152

(22) Filed: Feb. 20, 2020

(65) Prior Publication Data
US 2021/0259739 A1    Aug. 26, 2021

(51) Int. Cl.
*A61B 17/34* (2006.01)
*A61B 17/00* (2006.01)
*A61B 90/00* (2016.01)

(52) U.S. Cl.
CPC ...... *A61B 17/3494* (2013.01); *A61B 17/3423* (2013.01); *A61B 2017/00862* (2013.01); *A61B 2017/00991* (2013.01); *A61B 2090/036* (2016.02); *A61B 2217/005* (2013.01)

(58) Field of Classification Search
CPC .......... A61B 17/3423; A61B 2217/005; A61B 2017/00991; A61B 2017/3443; A61B 2017/00862; A61B 2017/3425; A61B 2017/3427; A61B 2017/345; A61B 2017/3429; A61B 2090/036; A61B 2090/08021; A61B 17/3497; A61B 17/00234; A61B 17/341; A61B 2218/008; A61B 1/32; A61B 17/0218; A61M 2039/0276; A61M 2039/0297; A61M 2039/0282; A61M 39/02; A61M 39/0247; A61M 2039/0626; A61M 29/00
USPC .......... 606/172; 604/332, 334, 338; 128/856; 600/201, 205
See application file for complete search history.

(56) References Cited

U.S. PATENT DOCUMENTS

| | | |
|---|---|---|
| 4,984,564 A | 1/1991 | Yuen |
| 5,007,926 A | 4/1991 | Derbyshire |
| 5,037,379 A | 8/1991 | Clayman et al. |
| 5,078,726 A | 1/1992 | Kreamer |
| 5,143,082 A | 9/1992 | Kindberg et al. |
| 5,159,921 A | 11/1992 | Hoover |

(Continued)

*Primary Examiner* — Tan-Uyen T Ho
*Assistant Examiner* — Bridget E. Rabaglia
(74) *Attorney, Agent, or Firm* — Carter, DeLuca & Farrell LLP

(57) ABSTRACT

A tissue guard includes a body having a first section and a second section each defining an open proximal end, an open distal end, and a lumen extending therethrough. The distal end of the first section includes a plurality of resilient fingers operably coupled thereto, each of the plurality of resilient fingers including a flange biased towards the distal end of the first section. The second section includes a corresponding plurality of holes defined therein in annular row-like spatial registration with the plurality of resilient fingers. The distal end of the second section is configured to be telescopically received within the proximal end of the first section such that mechanical engagement of the plurality of fingers with a corresponding row of annular holes locks the first section relative to the second section to incrementally adjust the height of the body.

20 Claims, 6 Drawing Sheets

(56) References Cited

U.S. PATENT DOCUMENTS

| | | |
|---|---|---|
| 5,171,262 A | 12/1992 | MacGregor |
| 5,176,659 A | 1/1993 | Mancini |
| 5,213,114 A | 5/1993 | Bailey, Jr. |
| 5,215,101 A | 6/1993 | Jacobs et al. |
| 5,215,521 A | 6/1993 | Cochran et al. |
| 5,224,930 A | 7/1993 | Spaeth et al. |
| 5,231,974 A | 8/1993 | Giglio et al. |
| 5,308,327 A | 5/1994 | Heaven et al. |
| 5,312,416 A | 5/1994 | Spaeth et al. |
| 5,330,483 A | 7/1994 | Heaven et al. |
| 5,354,303 A | 10/1994 | Spaeth et al. |
| 5,374,272 A | 12/1994 | Arpa et al. |
| 5,380,304 A | 1/1995 | Parker |
| 5,411,549 A | 5/1995 | Peters |
| 5,441,515 A | 8/1995 | Khosravi et al. |
| 5,449,382 A | 9/1995 | Dayton |
| 5,520,610 A | 5/1996 | Giglio et al. |
| 5,578,075 A | 11/1996 | Dayton |
| 5,611,803 A | 3/1997 | Heaven et al. |
| 5,618,296 A | 4/1997 | Sorensen et al. |
| 5,636,639 A | 6/1997 | Turturro et al. |
| 5,649,550 A | 7/1997 | Crook |
| 5,707,385 A | 1/1998 | Williams |
| 5,769,794 A | 6/1998 | Conlan et al. |
| 5,785,677 A | 7/1998 | Auweiler |
| 5,810,721 A | 9/1998 | Mueller et al. |
| 5,814,044 A | 9/1998 | Hooven |
| 5,906,577 A | 5/1999 | Beane et al. |
| 5,957,888 A | 9/1999 | Hinchliffe |
| 5,971,995 A | 10/1999 | Rousseau |
| 5,993,427 A | 11/1999 | Rolland et al. |
| 6,027,779 A | 2/2000 | Campbell et al. |
| 6,039,748 A | 3/2000 | Savage et al. |
| 6,048,309 A | 4/2000 | Flom et al. |
| 6,059,793 A | 5/2000 | Pagedas |
| 6,090,136 A | 7/2000 | McDonald et al. |
| 6,162,172 A | 12/2000 | Cosgrove et al. |
| 6,206,889 B1 | 3/2001 | Bennardo |
| 6,228,095 B1 | 5/2001 | Dennis |
| 6,258,102 B1 | 7/2001 | Pagedas |
| 6,350,267 B1 | 2/2002 | Stefanchik |
| 6,382,211 B1 | 5/2002 | Crook |
| 6,387,102 B2 | 5/2002 | Pagedas |
| 6,406,440 B1 | 6/2002 | Stefanchik |
| 6,814,700 B1 | 11/2004 | Mueller et al. |
| 7,547,310 B2 | 6/2009 | Whitfield |
| 7,670,346 B2 | 3/2010 | Whitfield |
| 7,691,120 B2 | 4/2010 | Shluzas et al. |
| 8,075,567 B2 | 12/2011 | Taylor et al. |
| 8,206,294 B2 | 6/2012 | Widenhouse et al. |
| 8,409,112 B2 | 4/2013 | Wynne et al. |
| 8,409,216 B2 | 4/2013 | Parihar et al. |
| 8,414,596 B2 | 4/2013 | Parihar et al. |
| 8,425,533 B2 | 4/2013 | Parihar et al. |
| 8,540,628 B2 | 9/2013 | O'Prey et al. |
| 8,579,914 B2 | 11/2013 | Menn et al. |
| 8,597,180 B2 | 12/2013 | Copeland et al. |
| 8,740,904 B2 | 6/2014 | Stopek |
| 8,777,849 B2 | 7/2014 | Haig et al. |
| 8,864,658 B2 | 10/2014 | Wilkins et al. |
| 8,961,408 B2 | 2/2015 | Wilkins et al. |
| 8,968,329 B2 | 3/2015 | Cabrera |
| 8,986,321 B2 | 3/2015 | Parihar et al. |
| 9,017,340 B2 | 4/2015 | Davis |
| 9,877,893 B2 | 1/2018 | Taylor et al. |
| 2005/0267492 A1 | 12/2005 | Poncet et al. |
| 2006/0200169 A1 | 9/2006 | Sniffin |
| 2006/0200170 A1 | 9/2006 | Aranyi |
| 2006/0200185 A1* | 9/2006 | Marchek ............ A61B 17/3421 606/191 |
| 2009/0287061 A1* | 11/2009 | Feigenbaum ....... A61B 17/3423 600/204 |
| 2010/0312189 A1 | 12/2010 | Shelton, IV et al. |
| 2011/0184311 A1 | 7/2011 | Parihar et al. |
| 2011/0190779 A1 | 8/2011 | Gell et al. |
| 2011/0282237 A1 | 11/2011 | Conlon |
| 2011/0319719 A1 | 12/2011 | O'Prey et al. |
| 2012/0083795 A1 | 4/2012 | Fleming et al. |
| 2012/0130177 A1* | 5/2012 | Davis ................. A61B 17/3423 600/201 |
| 2012/0130187 A1* | 5/2012 | Okoniewski ........ A61B 17/3423 600/208 |
| 2012/0157777 A1 | 6/2012 | Okoniewski |
| 2013/0178710 A1* | 7/2013 | Suh .................... A61B 17/0218 600/205 |
| 2013/0225933 A1* | 8/2013 | Kleyman ........... A61B 17/3423 600/208 |
| 2013/0325025 A1 | 12/2013 | Hathaway et al. |
| 2014/0052018 A1 | 2/2014 | Hawkins |
| 2019/0110786 A1* | 4/2019 | Ip ........................... A61B 17/02 |

\* cited by examiner

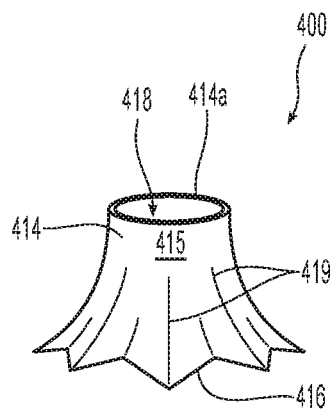
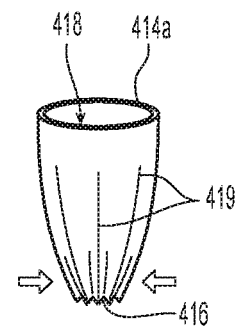
Fig. 4A	Fig. 4B
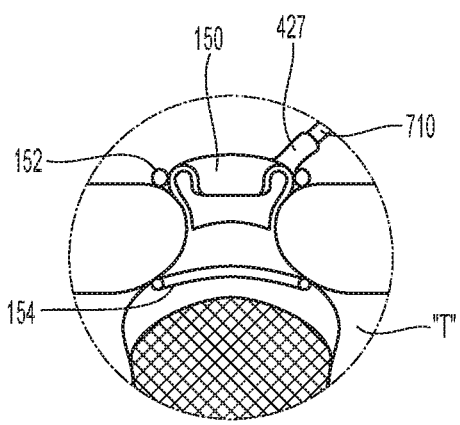
Fig. 5A
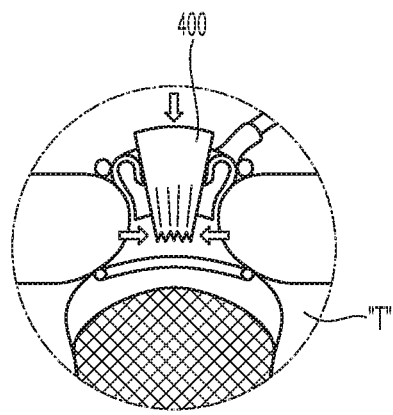
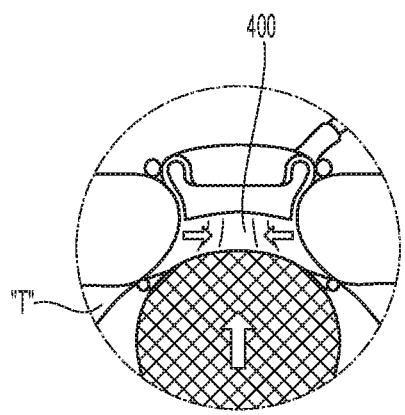
Fig. 5B	Fig. 5C

CUTTING GUARD

FIELD

The present disclosure relates to tissue specimen removal and, more particularly, to tissue guards and systems incorporating the same for use in tissue specimen removal procedures and other surgical procedures.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a tissue guard including a body having a first section and a second section each defining an open proximal end, an open distal end, and a lumen extending therethrough. The distal end of the first section includes a plurality of resilient fingers operably coupled thereto, each of the plurality of resilient fingers including a flange biased towards the distal end of the first section. The second section includes a corresponding plurality of holes defined therein in annular row-like spatial registration with the plurality of resilient fingers. The distal end of the second section is configured to be telescopically received within the proximal end of the first section such that mechanical engagement of the plurality of fingers with a corresponding row of annular holes locks the first section relative to the second section to incrementally adjust the height of the body.

In aspects according to the present disclosure, each flange of the plurality of fingers is movable between a first configuration to facilitate insertion of the second section within the first section and a second configuration wherein each flange of the plurality of fingers mechanically engages a corresponding hole of the corresponding plurality of holes. In other aspects according to the present disclosure, each flange of the plurality of fingers is biased towards the second configuration. In still other aspects according to the present disclosure, each flange of the plurality of fingers is configured to ratchet within successive holes of the corresponding plurality of holes when the first section is moved distally atop the second section to reduce the height of the body to a desired height.

In aspects according to the present disclosure, the first section of the body includes a proximal lip that extends inwardly towards the lumen to form an annular channel defined therein configured to direct surgical exhaust and surgical fluids from an operating cavity to a port defined in an outer peripheral surface of the lip. In other aspects according to the present disclosure, the lip includes a port defined therein adapted to connect to a fluid management system.

In aspects according to the present disclosure, the body of the tissue guard is made from a material resistant to cuts or tears from surgical instrumentation.

Provided in accordance with another embodiment of the present disclosure is a tissue guard including a body defining an open proximal end, an open distal end, and a lumen extending therethrough. The distal end of the body includes a plurality of folds extending proximally along a portion of a length of the body, the folds allowing the distal end of the body to selectively transition between a first configuration wherein the distal end of the body is compressed facilitating insertion of the body within an access device and a second configuration wherein the distal end of the body is substantially flared relative to the proximal end of the body to secure the body within the access device.

In aspects according to the present disclosure, at least the distal end of the body is made from a resilient material to facilitate transition between the first and second configurations. In other aspects according to the present disclosure, the proximal end of the body is adapted to mechanically engage an access device. In still other aspects according to the present disclosure, the proximal end of the body includes a connection port defined therein adapted to operably engage a fluid management system.

Provided in accordance with another embodiment of the present disclosure is a port connector for a tissue guard including a body having proximal and distal ends, the proximal end of the body adapted to operably connect to a fluid management system and the distal end of the body adapted to operably connect to a connection port of a tissue guard. An O-ring is adapted to mechanically engage an annular groove defined within the connection port, the O-ring ensuring a fluid tight operable connection between the distal end of the body and the connection port.

In aspects according to the present disclosure, the mechanical connection between the distal end of the body and the connection port permits 360 degree rotation of the port connector relative to the connection port while maintaining a fluid tight seal. In other aspects according to the present disclosure, the connection port is at least partially resilient to compensate for vertical movement between the connection port and the fluid management system.

In aspects according to the present disclosure, the distal and proximal ends of the body of the port connector are disposed at an angle relative to one another. In other aspects according to the present disclosure, the angle is in the range of about 10 degrees to about 75 degrees.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

FIG. 4A is perspective view of another embodiment of a tissue guard in accordance with the present disclosure shown in an expanded configuration;

FIG. 4B is a perspective view of the tissue guard of FIG. 4A shown in a compressed configuration;

FIGS. 5A-5C are various views of the tissue guard of FIG. 4A during installation thereof into an access device;

DETAILED DESCRIPTION

Figure 1A:
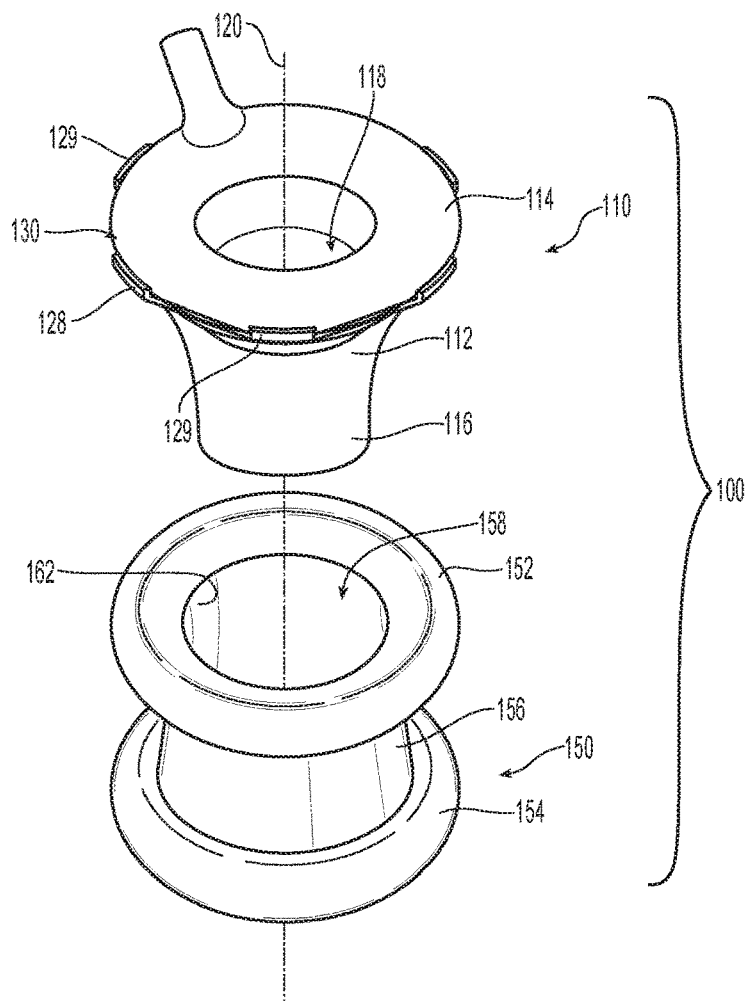
FIG. 1A is an exploded, top, perspective view of a system provided in accordance with the present disclosure including an access device and a tissue guard.
Figure 1B:
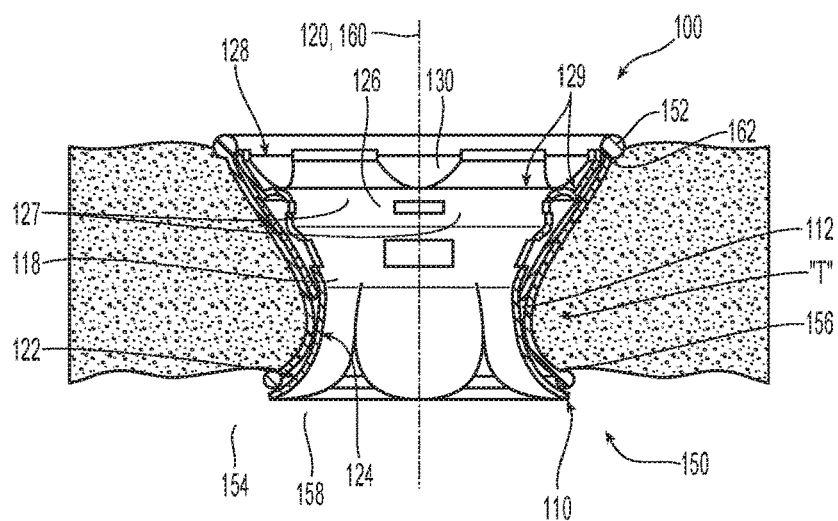
FIG. 1B is a cross-sectional view of the system of FIG. 1A disposed within an opening in tissue.

Turning to FIGS. 1A and 1B, a system 100 provided in accordance with the present disclosure includes a tissue guard 110 and an access device 150. Tissue guard 110 is monolithically formed as a single piece of material, e.g., a biocompatible plastic such as, for example, polyethylene, polycarbonate, etc., from any suitable method, e.g., injection molding. The material, thickness, and configuration of tissue guard 110 are such that tissue guard 110 defines sufficient stiffness to maintain its shape when positioned within an opening in tissue "T" and/or when engaged within access device 150. However, the material, thickness, and configuration of tissue guard 110 also provide sufficient resilient flexibility to permit manipulation of tissue guard 110 from an at-rest position for insertion into an opening in tissue "T" and/or for engagement within access device 150, with tissue guard 110 returning to or towards the at-rest position after insertion and/or engagement as explained in more detail below. Further, the material, thickness, and configuration of tissue guard 110 is selected such that tissue guard 110 is configured to withstand cutting and puncturing by surgical knives, scalpels, pencils, and the like, thereby protecting surrounding tissue "T" and/or access device 150 from being cut or punctured. Tissue guard 110 may additionally or alternatively be configured to inhibit transfer of thermal and/or electrical energy therethrough to protect surrounding tissue "T" and/or access device 150 from thermal and/or electrical energy.

Continuing with reference to FIGS. 1A and 1B, tissue guard 110 includes a body 112 defining an open proximal end 114, an open distal end 116, and a lumen 118 extending therethrough between open proximal and distal ends 114, 116, respectively. Lumen 118 defines a longitudinal axis 120 and is configured to receive one or more surgical instruments (not shown) therethrough. In embodiments, body 112 defines a funnel-shaped configuration wherein a diameter of body 112 at open proximal end 114 thereof is greater than a diameter of body 112 at open distal end 116 thereof. Additionally or alternatively, the exterior surface 122 of body 112 may define a generally concave configuration while the interior surface 124 of body 112, which defines lumen 118, may define a generally convex configuration.

Access device 150 may be configured as a tissue retractor, an access port, or other suitable access device configured for positioning within an opening in tissue "T," e.g., a surgical incision or a naturally-occurring orifice, to provide access therethrough into an internal surgical site. Access device 150 includes a proximal rim 152 configured for positioning on an external side of the opening in tissue "T," a distal rim 154 configured for positioning on an internal side of the opening in tissue "T," and a body 156 extending between proximal and distal rims 152, 154, respectively. Body 156 is configured to extend through the opening in tissue "T" and defines a passageway 158 extending longitudinally therethrough to permit access to an internal surgical site through the opening in tissue "T." Passageway 158 defines a longitudinal axis 160. At least a portion of body 156 of access device 150 may be flexible to facilitate insertion and positioning of access device 150 within the opening in tissue "T." In embodiments, body 156 is formed from a flexible sleeve of material including one or more layers of material. Further, access device 150 may be selectively adjustable, e.g., by rolling proximal rim 154 distally about body 156, to retract tissue "T" and/or secure access device 150 within the opening in tissue "T." Access device 150 may further define an inwardly-extending overhang 162 between proximal rim 154 and body 156 and extending annularly about passageway 158.

As shown in FIG. 1B, in use, access device 150 is positioned within an opening in tissue "T" such that, as noted above, distal rim 154 is disposed on an internal surface of tissue "T" on the internal side of the opening in tissue "T," body 156 extends through the opening in tissue "T," and proximal rim 152 is disposed on an exterior surface of tissue "T" on the external side of the opening in tissue "T." As also noted above, access device 150 may be adjusted to conform access device 150 to a patient's anatomy, retracting tissue "T" and/or securing access device 150 within the opening in tissue "T." With access device 150 disposed within the opening in tissue "T," tissue guard 110, led by open distal end 116 thereof, is inserted into passageway 158.

Figure 2:
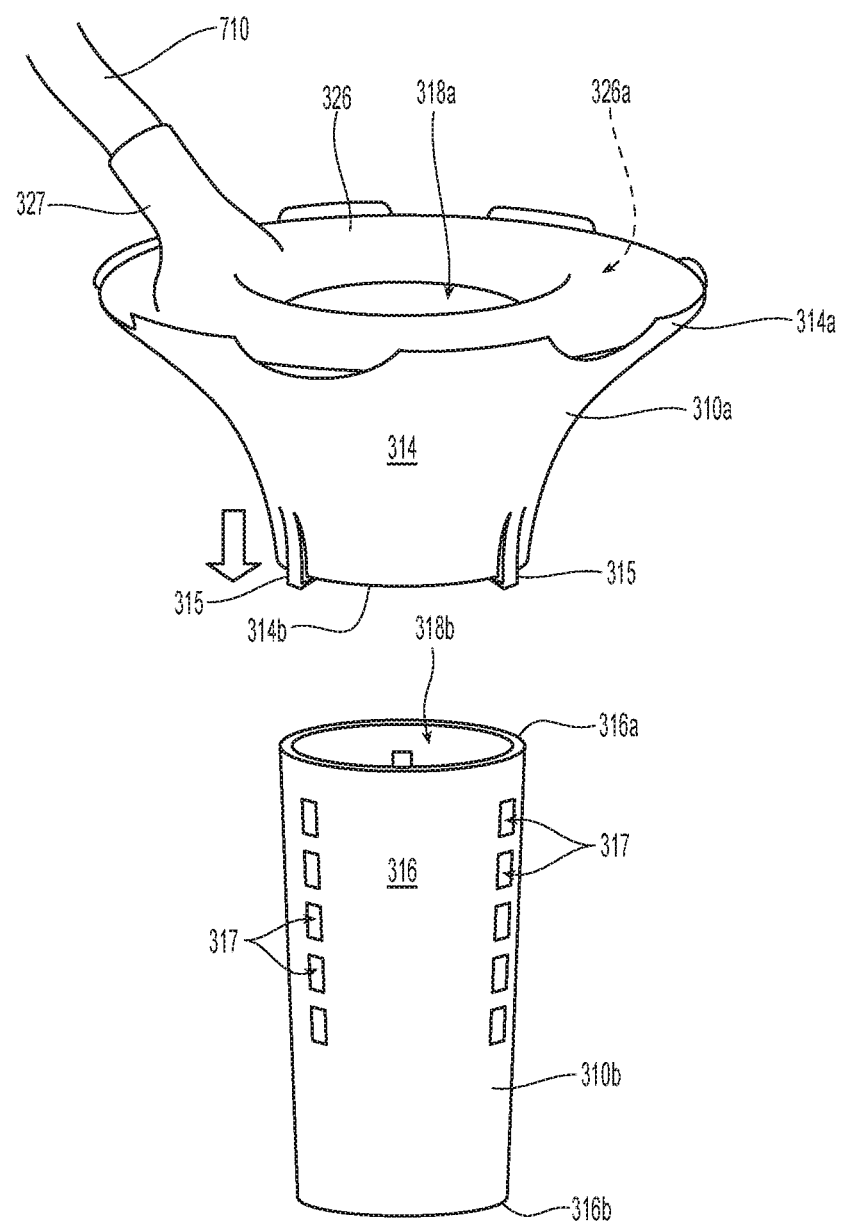
FIG. 2 is an exploded, perspective view of a tissue guard in accordance with an embodiment of the present disclosure.
Figure 3A:
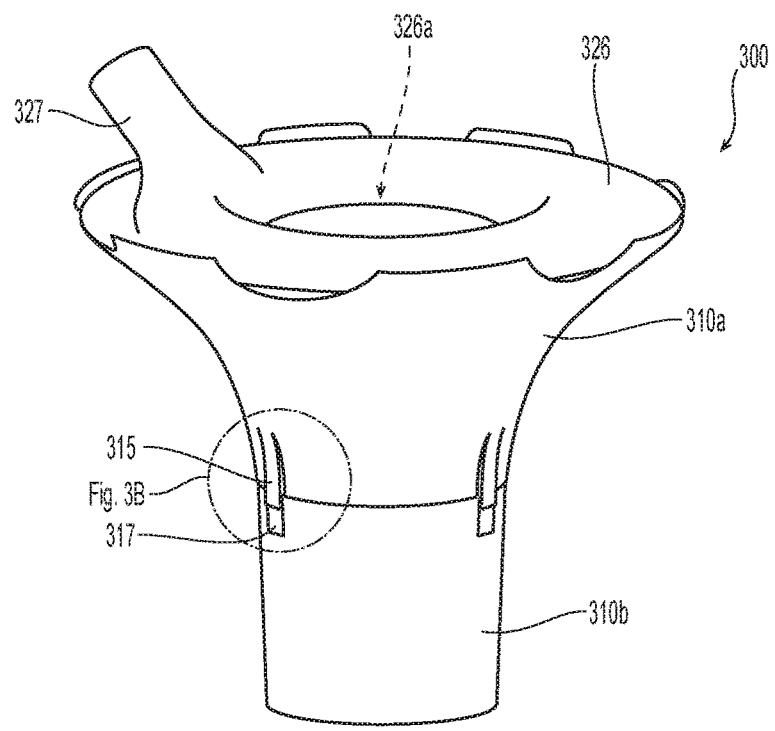
FIG. 3A is perspective view the tissue guard of FIG. 2 in an assembled condition.
Figure 3B:
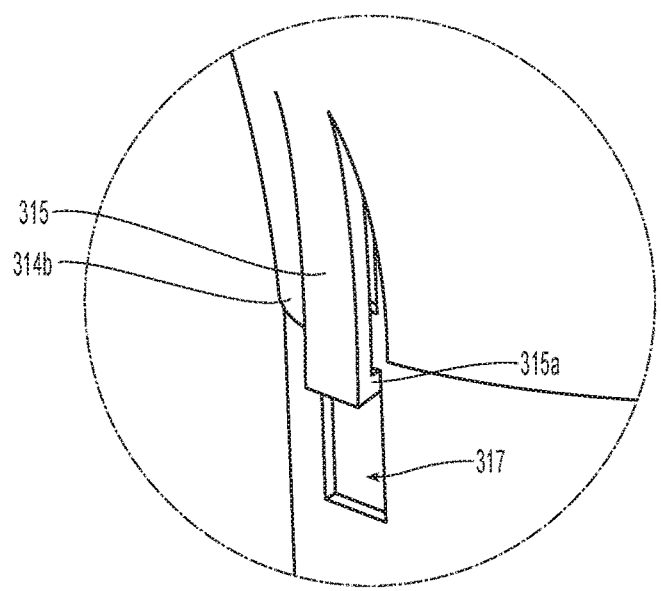
FIG. 3B is a greatly-enlarged view showing the area of detail of FIG. 3A.

Turning now to FIGS. 2-3B, another embodiment of a tissue guard is disclosed and is represented as tissue guard 300. Tissue guard 300 includes first and second sections 310a and 310b that selectively couple together to form tissue guard 300. First section 310a of tissue guard 300 includes a body 314 having proximal and distal ends 314a and 314b, respectively, and second section 310b includes a body 316 having proximal and distal ends 316a and 316b, respectively. Proximal end 314a of first section 310a is configured to mechanically engage rim 152 of access device 150, e.g., proximal end 314a may mechanically seat under rim 152 to secure the tissue guard 300 therein.

Figure 7:
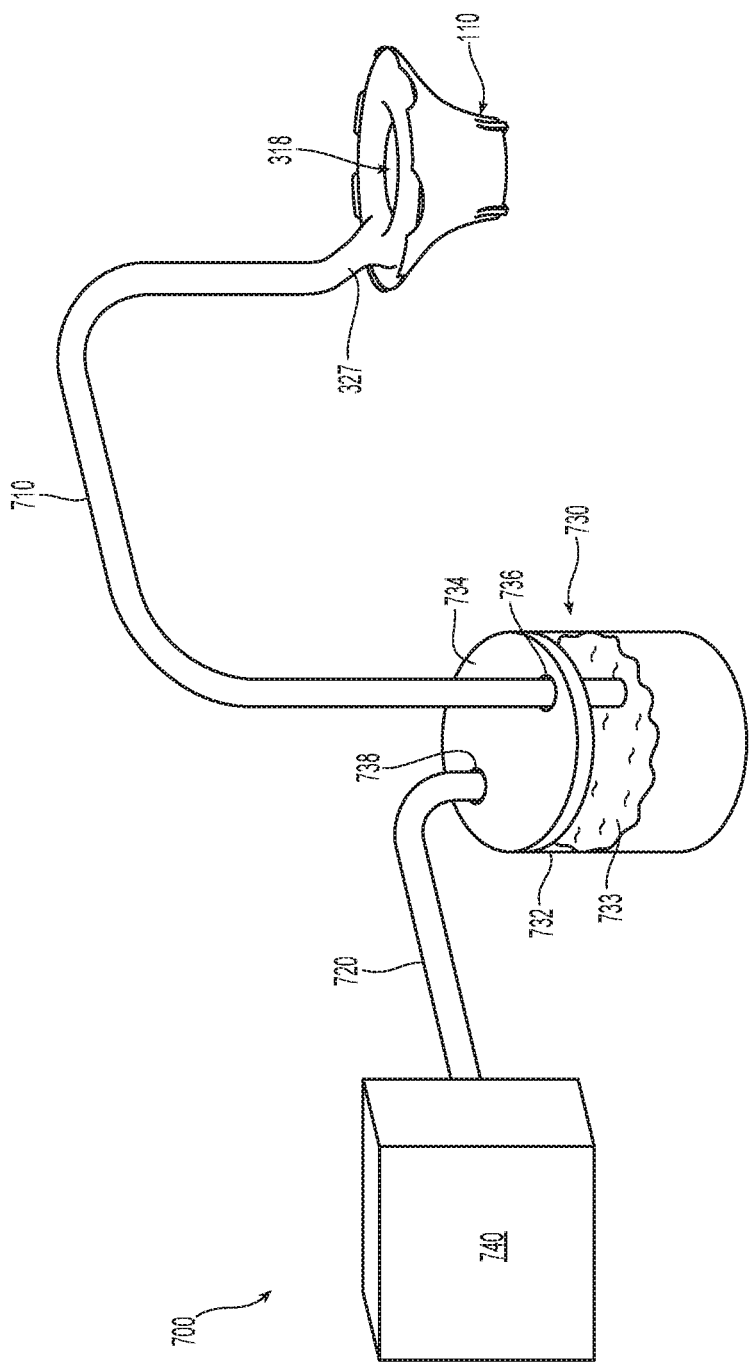
FIG. 7 is a system provided in accordance with the present disclosure including the tissue guard of FIG. 2, tubing, a collection reservoir, and a smoke evacuation source.

First section 310a of body 314 also includes proximal rim 326 defining an annular channel 326a therein formed at a proximal end thereof that is configured to direct surgical gases and fluids from within the surgical site to a fluid or smoke evacuation collection system 700 as explained in more detail below (See FIG. 7). An evacuation port or connection 327 is disposed in fluid communication with the annular channel 326a and extends from the proximal rim 326 for ultimate connection to tubing 710 of the evacuation system 700 (FIG. 7).

Body 316 of section 310b is configured to telescopically engage body 314 of section 310a. More particularly, the distal end of section 310a is configured to receive the proximal end 316a of section 310b. Or the distal end 316b of section 310b may be inserted through the proximal end 314a of section 310a. Each section 310a, 310 may be tapered for this purpose. When the two sections 310a, 310b are engaged, corresponding instrument lumens 318a, 318b defined within respective sections 310a, 310b align for surgical access to the operating cavity.

The distal end 314b of body 314 includes one or a plurality of resilient fingers 315 extending therefrom (See FIG. 3B). Fingers 315 are attached to the distal end 314b in a manner to bias inwardly towards body 314. Each finger 315 includes a flange 315a at a distal tip thereof that is configured to mechanically interface with a corresponding one of a plurality of holes 317 defined within body 316 of second section 310b. More particularly, a corresponding group or row of holes 317 extend around the outer surface of body 316 to match the number of fingers 315 extending from body 314. Additional rows of holes 317 extend distally towards the distal end 316b of body 316.

The mechanical engagement of each successive row of holes 317 with each group of fingers 315 allows the height of the assembled tissue guard 300 to be selectively sized according to a particular surgical purpose. In other words, section 310b may be inserted into section 310a or section 310a may be pushed distally atop section 310b at incremental stages to adjust the height of the tissue guard 300 as needed. As section 310b is pulled into section 310a, the fingers 315 flex initially outwardly and then bias inwardly to ratchet to engage successive groups of holes 317 to lock the sections 310a, 310b relative to one another at a desired position. Flanges 315a of finger 315 may include one or more angled surfaces to facilitate ratcheting and/or facilitate disengagement of the two sections 310a, 310b. The fingers 315 and flanges 315a may be angled differently depending on the particular engagement of the two sections 310a, 310b and the relative intended motion therebetween. Each flange 315a of each finger 315 is configured to ratchet within successive holes 317 when the first section 310a is moved distally atop the second section 310 (or section 310b is moved proximally within section 310a) to reduce the height of the tissue guard 300 to a desired height.

As mentioned above, lip 326 defines an annular channel 326a therein configured to direct surgical exhaust from the surgical site. As explained in more detail below, port 327 is configured to connect to exhaust tubing 710 of a fluid management or smoke evacuation system 700 (FIG. 7). In other words, lip 326 is configured as generally hollow sleeve disposed proximate the inner peripheral surface of proximal end 314 of tissue guard 300 and is configured to direct evacuation fluids and smoke to the exhaust tubing 710 and to the fluid management or smoke evacuation system 700.

With tissue guard 300 engaged within access device 150 as detailed above, surgical instrumentation may be inserted therethrough into the internal surgical site to, for example, extract a tissue specimen therefrom. Tissue guard 300, as noted above, protects tissue "T" as well as access device 150 during the insertion, manipulation, use and withdrawal of any such surgical instrumentation.

Turning no to FIGS. 4A-5C, another embodiment of a tissue guard is shown and is represented as tissue guard 400. With additional momentary reference to FIG. 2-3B, tissue guard 400 includes elements similar to tissue guard 300 except as explicitly contradicted below and may be used in conjunction with access device 150 as part of a system similar to system 100. For purposes of brevity, only differences between tissue guard 400 and tissue guard 300 are detailed below, while similarities are summarily described or omitted.

Tissue guard 400 includes a body 415 having proximal and distal ends 414 and 416, respectively, that define an internal lumen 418 therebetween for accessing a surgical cavity. Proximal end 414 includes a lip 414a that is configured to mechanical engage rim 152 of access device as described above. Body 415 is substantially tapered such that distal end 416 is generally larger than proximal end 414 allowing the tissue guard 400 to properly seat within access device 150. In this regard, body 415 is made from a resilient material and includes a series of folds 419 extending at least partially along the body from proximal end 414 to distal end 416 that allow the body 415 to be compressed (FIG. 4B).

As shown in FIGS. 5A-5C, folds 419 allow the body 415 to be compressed at the distal end 416 thereof to facilitate insertion into the access device 150. Once inserted, the body 415 and folds 419 may be released allowing the body 415 to expand within the access device 150 to conform with the interior peripheral surface of the lumen 156 of the access device 150. The bias of the resilient material of the body 415 of the tissue guard 400 maintains the tissue guard 400 in place as needed. As mentioned above, the proximal end 414 may include a lip 414a that mechanically engages rim 152 of the access device 150 to ensure engagement.

With tissue guard 400 engaged within access device 150 as detailed above, surgical instrumentation may be inserted through lumen 418 of tissue guard 400 into the internal surgical site to, for example, extract a tissue specimen therefrom. Tissue guard 400, as noted above, protects tissue "T" as well as access device 150 during the insertion, manipulation, use and withdrawal of any such surgical instrumentation.

Turning momentarily to FIG. 7, smoke evacuation system 700 is provided in accordance with the present disclosure and is shown generally including tissue guard 300, tubing 710, 720, a collection reservoir 730, and a smoke evacuation (or vacuum) source 740. Tissue guard 400 works with smoke evacuation system 700 in a similar fashion. Tissue guard 300 and tubing 710 are detailed above and are coupled to one another, e.g., via engagement of one end of tubing 710 about port 327 of tissue guard 300. The other end of tubing 710 extends into collection reservoir 730 in sealing relation therewith.

Collection reservoir 730 includes a base 732 and a lid 734 sealed about base 732. Lid 734 defines first and second ports 736, 738 configured to receive ends of tubing 710, 720, respectively, in sealing relation therewith. These ends of tubing 710, 720 extend into the interior volume 733 of base 732 and are spaced-apart from one another as well as the bottom of base 732. Tubing 720 extends from collection reservoir 730 to smoke evacuation source 740 wherein the other end of tubing 720 is coupled to smoke evacuation source 740. In this manner, upon activation of smoke evacuation source 740, suction is established through rim 326 of tissue guard 300, tubing 710, collection reservoir 730, tubing 720, to smoke evacuation source 740. During use, this suction, in addition to evacuating smoke from tissue guard 300, may also suction liquids, tissue, and/or debris through tubing 710. However, as a result of the ends of tubing 710, 720 being spaced-apart from one another within collection reservoir 730 and spaced-apart from the bottom of base 732 of collection reservoir 730, the liquids, tissue, and/or debris are suctioned into collection reservoir 730 and deposited therein, while only the smoke and other gaseous fluids are further suctioned from collection reservoir 730 through tubing 720 to smoke evacuation source 740. As such, smoke evacuation source 740 is protected by inhibiting suctioning of liquids, tissue, and/or debris into smoke evacuation source 740.

Figure 6A:
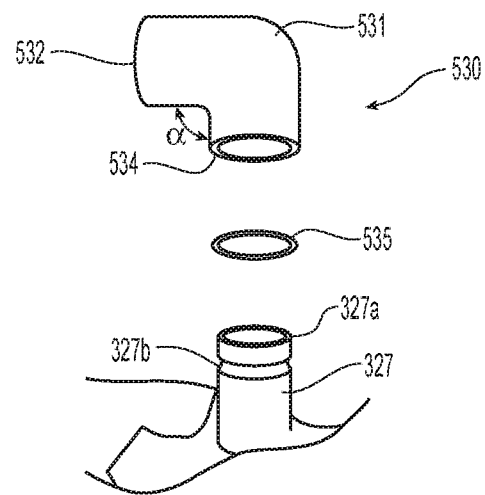
FIGS. 6A-6C are various views of a swivel port connector for use with the tissue guards of FIGS. 2 and 4A.
Figure 6B:
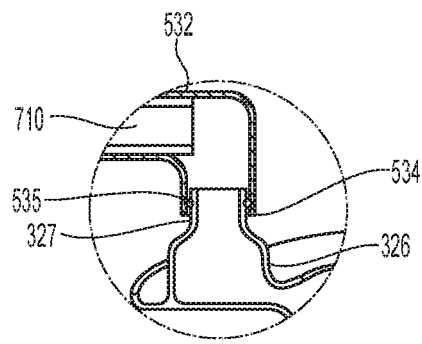
Figure 6C:
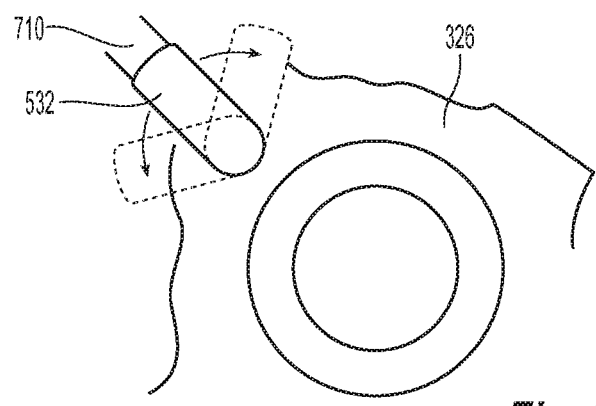

FIGS. 6A-6C show an embodiment of a swivel connector 530 for use with smoke evacuation system 700. Swivel connector 530 includes a body 531 having proximal and distal ends 532 and 534, respectively. Proximal end 532 connects to tubing 710 in any manner known in the art, e.g., friction-fit, clamp ring, etc. Distal end 534 connects to port 327 of tissue guard 300. More particularly, distal end 534 is dimensioned to encapsulate a top end 327a of port 327 of tissue guard 300 in a friction-fit manner. An O-ring 535 may be utilized to provide a fluid-tight seal therebetween. O-ring 535 may be dimensioned to seat within an annular groove 327b defined in port 327 (See FIG. 6B).

As shown in FIG. 6C, once the connector 530 is coupled to port 327, any lateral movement of the tubing 710 will be compensated by movement of the swivel connector 530 to reduce the likelihood of a disconnection from the evacuation system 700. More particularly, the mechanical connection between the distal end of the connector 530 and the connection port 327 permits 360 degree rotation of the port connector 530 relative to the connection port 327 while maintaining a fluid tight seal. Port 327 may be resilient to compensate for vertical movement between the tissue guard 300 and the evacuation system 700. Moreover, the connector 530 facilitates relocation of the tubing 710 out of the way of the surgeon and surgical instrumentation during operating conditions. This reduces tangling and improves visibility to the operating site.

The connector 530 and the port 327 may be disposed at an angle alpha (λ) relative to one another (FIG. 6A). Angle alpha (λ) may be in the range of about 10 degrees to about 75 degrees.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue guard, comprising:
a body including a first section and a second section each defining an open proximal end, an open distal end, and a lumen extending therethrough, the distal end of the first section including a plurality of resilient fingers operably coupled thereto, each of the plurality of resilient fingers including a flange biased towards the distal end of the first section, the second section including a plurality of holes defined therein, the plurality of holes being axially and radially spaced relative to each other in longitudinal and annular rows, the longitudinal rows being in registration with the plurality of resilient fingers, the proximal end of the second section configured to be telescopically received within the distal end of the first section such that mechanical engagement of the plurality of resilient fingers with one of the annular rows of the plurality of holes locks the first section relative to the second section to incrementally adjust the height of the body.

2. The tissue guard according to claim 1, wherein each flange of the plurality of resilient fingers is movable between a first configuration to facilitate insertion of the second section within the first section and a second configuration wherein each flange of the plurality of resilient fingers mechanically engages one of the plurality of holes.

3. The tissue guard according to claim 2, wherein each flange of the plurality of resilient fingers is biased towards the second configuration.

4. The tissue guard according to claim 1 wherein each flange of the plurality of resilient fingers is configured to ratchet within successive holes in one of the longitudinal rows of the plurality of holes when the first section is moved distally atop the second section to reduce the height of the body to a desired height.

5. The tissue guard according to claim 1, wherein the first section of the body includes a proximal lip that extends inwardly towards the lumen to form an annular channel configured to direct surgical exhaust and surgical fluids from an operating cavity to a port defined in an outer peripheral surface of the proximal lip.

6. The tissue guard according to claim 5, wherein the port is adapted to connect to a fluid management system.

7. The tissue guard according to claim 1, wherein the body of the tissue guard is made from a material resistant to cuts or tears from surgical instrumentation.

8. The tissue guard according to claim 1, wherein the plurality of holes is defined through the second section from an outer surface to an inner surface defining the lumen.

9. The tissue guard according to claim 1, wherein the flanges of the plurality of resilient fingers extend distally beyond the distal end of the first section.

10. A system, comprising:
the tissue guard of claim 1; and
an access device including a body defining a passageway extending longitudinally through the body,
the tissue guide being positionable within the passageway of the access device.

11. The system according to claim 10, wherein the access device includes proximal and distal rims, and the body of the access device extends between the proximal and distal rims.

12. The system according to claim 11, wherein the access device includes an inwardly-extending overhang between the proximal rim and the body, the inwardly-extending overhang extending annularly about the passageway.

13. A system, comprising:
the tissue guard of claim 5; and
a fluid management system including a collection reservoir and a smoke evacuation source,
the port of the tissue guard is coupled to the fluid management system.

14. The system according to claim 13, wherein the smoke evacuation source is a vacuum.

15. The system according to claim 13, wherein the fluid management system includes a first tube interconnecting the collection reservoir and the port of the tissue guard, and a second tube interconnecting the collection reservoir and the smoke evacuation source.

16. The system according to claim 13, further including a port connector including a body having proximal and distal ends, the proximal end of the body adapted to operably connect to the fluid management system and the distal end of the body adapted to operably connect to the port of the tissue guard.

17. The system according to claim 16, wherein the port connector includes an O-ring adapted to mechanically engage an annular groove defined within the port, the O-ring ensuring a fluid tight operable connection between the distal end of the body and the port.

18. The system according to claim 16, wherein the mechanical connection between the distal end of the body and the port permits 360-degree rotation of the port connector relative to the port while maintaining a fluid tight seal.

19. The system according to claim 16, wherein the distal and proximal ends of the body of the port connector are disposed at an angle relative to one another.

20. The system according to claim 19, wherein the angle is in the range of about 10 degrees to about 75 degrees.

* * * * *